United States Patent
Jager et al.

(10) Patent No.: US 6,774,226 B1
(45) Date of Patent: Aug. 10, 2004

(54) ISOLATED NUCLEIC ACID MOLECULES ENCODING CANCER ASSOCIATED ANTIGENS, THE ANTIGENS PER SE, AND USES THEREOF

(75) Inventors: Dirk Jager, New York, NY (US); Elizabeth Stockert, New York, NY (US); Matthew Scanlan, New York, NY (US); Ali Gure, New York, NY (US); Elke Jager, Frankfurt am Main (DE); Alexander Knuth, Frankfurt am Main (DE); Lloyd Old, New York, NY (US); Yao-tseng Chen, New York, NY (US)

(73) Assignees: Ludwig Institute for Cancer Research, New York, NY (US); Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/451,739

(22) Filed: Nov. 30, 1999

(51) Int. Cl.[7] .................. C07H 21/04; C12N 15/00; C12N 5/00
(52) U.S. Cl. .............. 536/23.5; 435/320.1; 435/325
(58) Field of Search .................. 536/23.5, 23.1; 435/320.1, 325

(56) References Cited

U.S. PATENT DOCUMENTS 6,255,470 B1 * 7/2001 Chen et al. ............... 536/23.1
6,500,942 B1 * 12/2002 Tam et al. ................. 536/23.5

FOREIGN PATENT DOCUMENTS

WO    WO 9721809 A1 * 6/1997  ........... C12N/15/12

OTHER PUBLICATIONS

Jäger, et al, "Cancer–Testis Antigens and INGI Tumor Suppressor Gene Product Are Breast Cancer Antigens: Characterization of Tissue–specific INGI Transcripts and a Homologous Gene, " Canc. Res, 59:6197–6204 (Dec. 15, 1999 (Not Prior art)).

* cited by examiner

Primary Examiner—Gary Nickol
(74) Attorney, Agent, or Firm—Fulbright & Jaworski LLP

(57) ABSTRACT

The invention relates to newly identified cancer associated antigens. It has been discovered that each of these molecules provokes antibodies when expressed by a subject. The ramifications of this observation are also a part of this invention.

18 Claims, No Drawings

ISOLATED NUCLEIC ACID MOLECULES ENCODING CANCER ASSOCIATED ANTIGENS, THE ANTIGENS PER SE, AND USES THEREOF

FIELD OF THE INVENTION

This invention relates to antigens associated with cancer, the nucleic acid molecules encoding them, as well as the uses of these.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

Two basic strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., 0. Mandelboim, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}Cr$ release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. Pat. No. 5,698,396, and application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

This methodology has been applied to a range of tumor types, including those described by Sahin et al., supra, and Pfreundschuh, supra, as well as to esophageal cancer (Chen et al., Proc. Natl. Acad. Sci. USA 94: 1914–1918 (1997)); lung cancer (Güre et al., Cancer Res. 58: 1034–1041 (1998)); colon cancer (Ser. No. 08/948, 705 filed Oct. 10, 1997 now U.S. Pat. No. 6,043,084, incorporated by reference, and so forth. Among the antigens identified via SEREX are the SSX2 molecule (Sahin et al., Proc. Natl. Acad. Sci. USA 92: 11810–11813 (1995); Tureci et al., Cancer Res. 56: 4766–4772 (1996); NY-ESO-1 Chen, et al., Proc. Natl. Acad. Sci. USA 94: 1914–1918 (1997); and SCP 1 (Ser. No. 08/892,705 filed Jul. 15, 1997 now U.S. Pat. No, 6,138,123) incorporated by reference. Analysis of SEREX identified antigens has shown overlap between SEREX defined and CTL defined antigens. MAGE-1, tyrosinase, and NY-ESO-1 have all been shown to be recognized by patient antibodies as well as CTLs, showing that humoral and cell mediated responses do act in concert.

It is clear from this summary that identification of relevant antigens via SEREX is a desirable aim. The inventors have applied this methodology and have identified several new antigens associated with cancer, as detailed in the description which follows.

DETAILED DESCRIPTION OF PREFERRED EMBODIMENTS

Example 1

The SEREX methodology, as described by, e.g. Sahin, et al., Proc. Natl. Acad. Sci. USA 92: 11810–11813 (1995); Chen, et al., Proc. Natl. Acad. Sci. USA 94: 1914–1918 (1997), and U.S. Pat. No. 5,698,396, all of which are incorporated by reference. In brief, total RNA was extracted from a sample of a cutaneous metastasis of a breast cancer patient (referred to as "BR11" hereafter), using standard CsCl guanidine thiocyanate gradient methodologies. A cDNA library was then prepared, using commercially available kits designed for this purpose. Following the SEREX methodology referred to supra, this cDNA expression library was amplified, and screened with either autologous BR11 serum which had been diluted to 1:200, or with allogeneic, pooled serum, obtained from 7 different breast cancer patients, which had been diluted to 1:1000. To carry out the screen, serum samples were first diluted to 1:10, and then preabsorbed with lysates of E. coli that had been transfected with naked vector, and the serum samples were then diluted to the levels described supra. The final dilutions were incubated overnight at room temperature with nitrocellulose membranes containing phage plaques, at a density of 4–5000 plaque forming units ("pfus") per 130 mm plate.

Nitrocellulose filters were washed, and incubated with alkaline phosphatase conjugated, goat anti-human Fcγ secondary antibodies, and reactive phage plaques were visualized via incubation with 5-bromo-4-chloro-3-indolyl phosphate and nitroblue tetrazolium.

This procedure was also carried out on a normal testicular cDNA library, using a 1:200 serum dilution.

A total of $1.12 \times 10^6$ pfus were screened in the breast cancer cDNA library, and 38 positive clones were identified. With respect to the testicular library, $4 \times 10^5$ pfus were screened, and 28 positive clones were identified.

Additionally, $8 \times 10^5$ pfus from the $BR_{11}$ cDNA library were screened using the pooled serum described. Of these, 23 were positive.

The positive clones were subdloned, purified, and excised to forms suitable for insertion in plasmids. Following amplification of the plasmids, DNA inserts were evaluated via restriction mapping (EcoRI-XbaI), and clones which represented different cDNA inserts were sequenced using standard methodologies.

If sequences were identical to sequences found in GenBank, they were classified as known genes, while sequences which shared identity only with ESTs, or were identical to nothing in these data bases, were designated as unknown genes. Of the clones from the breast cancer library which were positive with autologous serum, 3 were unknown genes. Of the remaining 35, 15 were identical to either NY-ESO-1, or SSX2, two known members of the CT antigen family described supra, while the remaining clones corresponded to 14 known genes. Of the testicular library, 12 of the clones were SSX2.

The NY-ESO-1 antigen was not found, probably because the commercial library that was used had been size fractionated to have an average length of 1.5 kilobases, which is larger than full length NY-ESO-1 cDNA which is about 750 base pairs long.

With respect to the screening carried out with pooled, allogeneic sera, four of the clones were NY-ESO-1. No other CT antigens were identified. With the exception of NY-ESO-1, all of the genes identified were expressed universally in normal tissue.

A full listing of the isolated genes, and their frequency of occurrence follows, in tables 1, 2 and 3. Two genes were found in both the BR11 and testicular libraries, i.e., poly (ADP-ribose)polymerase, and tumor suppression gene ING1. The poly (ADP-ribose)polymerase gene has also been found in colon cancer libraries screened via SEREX, as is disclosed by Scanlan, et al., Int. J. Cancer 76: 652–58 (1998) when the genes identified in the screening of the BR11 cDNA library by autologous and allogeneic sera were compared, NY-ESO-1 and human keratin.

TABLE 1

SEREX-defined genes identified by autologous screening of BR11 cDNA library

| Gene group | No. of clones | Comments | Expression |
|---|---|---|---|
| CT genes | 10 | NY-ESO-1 | tumor, testis |
|  | 5 | SSX2 | tumor, testis |
| Non-CT genes | 5 | Nuclear Receptor Co-Repressor | ubiquitous |
|  | 4 | Poly(ADP-ribose) polymerase | ubiquitous |
|  | 2 | Adenylosuccinatelyase | ubiquitous |
|  | 2 | cosmid 313 (human) | ESTs: muscle, brain, breast |
|  | 1 | CD 151 (trans-membrane protein) | ubiquitous |
|  | 1 | Human HRY Gen | RT-PCR: multiple normal tissues |
|  | 1 | Alanyl-t-RNA-Synthetase | ubiquitous |
|  | 1 | NAD(+) ADP-Ribosyltransferase | ubiquitous |
|  | 1 | Human keratin 10 | ESTs: multiple normal tissues |
|  | 1 | Human EGFR kinase substrate | ubiquitous |
|  | 1 | ING 1 Tumor suppressor gene | RT-PCR: multiple normal tissues |
|  | 1 | Unknown gene, NCI_CGAP_Pr12 cDNA clone | ESTs: pancreas, liver, spleen, uterus |
|  | 1 | Unknown gene | ESTs: multiple normal tissues |
|  | 1 | Unknown gene | RT-PCR: multiple normal tissues |

TABLE 2

SEREX-defined genes identified by allogeneic screening of BR11 cDNA library

| Gene group | No. of clones | Comments | Expression |
|---|---|---|---|
| CT genes | 4 | NY-ESO-1 | tumor, testis |
| Non-CT genes | 6 | zinc-finger helicase | ESTs: brain, fetal heart, total fetus |
|  | 4 | Acetoacetyl-CoA-thiolase | ubiquitous |
|  | 3 | KIAA0330 gene | ESTs: multiple normal tissues |
|  | 2 | U1snRNP | ubiquitous |
|  | 1 | Human aldolase A | ubiquitous |
|  | 1 | Retinoblastoma binding protein 6 | ESTs: tonsils, fetal brain, endothelial cells, brain |
|  | 1 | α2-Macroglobulin receptor associated protein | ubiquitous |
|  | 1 | Human Keratin 10 | ESTs: multiple normal tissues |

TABLE 3

SEREX-defined genes identified by screening of a testicular cDNA library with BR11 serum

| Gene group | No. of clones | Comments | Expression |
|---|---|---|---|
| CT genes: | 12 | SSX2 | tumor, testis |
| Non-CT genes: | 3 | Rho-associated coiled-coil forming protein | ubiquitous |
|  | 3 | Poly(ADP-ribose) polymerase | ubiquitous |

TABLE 3-continued

SEREX-defined genes identified by screening of a testicular cDNA library with BR11 serum

| Gene group | No. of clones | Comments | Expression |
|---|---|---|---|
| | 3 | Gene from HeLa cell, similar to TITIN | ubiquitous |
| | 2 | Gene from parathyroid tumor | RT-PCR: multiple normal tissues |
| | 1 | Transcription termination factor I-interacting peptide 21 | ubiquitous |
| | 1 | Gene from fetal heart | ESTs: multiple normal tissues |
| | 1 | ING 1 tumor suppressor gene | RT-PCR: multiple normal tissues |
| | 1 | KIAA0647 cDNA | ESTs: multiple normal tissues |
| | 1 | KIAA0667 cDNA | ESTs: multiple normal tissues |

Example 2

The mRNA expression pattern of the cDNAs identified in example 1, in both normal and malignant tissues, was studied. To do this, gene specific oligonucleotide primers were designed which would amplify cDNA segments 300–600 base pairs in length, using a primer melting temperature of 65–70° C. The primers used for amplifying MAGE-1,2,3 and 4, BAGE, NY-ESO-1, SCP1, and SSX1, 2, 3, 4 and 5 were known primers, or were based on published sequences. See Chen, et al. supra; Tureci, et al., Proc. Natl. Acad. Sci. USA 95: 5211–16(1998). Gure, et al., Int. J. Cancer 72: 965–71 (1997); Chen, et al., Proc. Natl. Acad. Sci. USA 91: 1004–1008 (1994); Gaugler, et al., J. Exp. Med. 179: 921–930(1994), dePlaen, et al., Immunogenetics 40: 360–369 (1994), all of which are incorporated by reference. RT-PCR was carried out for 35 amplification cycles, at an annealing temperature of 60° C. Using this RT-PCR assay, the breast cancer tumor specimen was positive for a broad range of CT antigens, including MAGE-1,3 AND 4, BAGE, SSX2, NY-ESO-1 and CT7. The known CT antigens SCP-1, SSX1, 4 and 5 were not found to be expressed.

An additional set of experiments were carried out, in which the seroreactivity of patient sera against tumor antigens was tested. Specially, ELISAs were carried out, in accordance with Stockert, et al., J. Exp. Med. 187: 1349–1354 (1998), incorporated by reference, to determine if antibodies were present in the patient sera. Assays were run for MAGE-1, MAGE-3, NY-ESO-1, and SSX2. The ELISAs were positive for NY-ESO-1 and SSX2, but not the two MAGE antigens.

Example 3

Two clones (one from the breast cancer cDNA library and one from the testicular library), were identified as a gene referred to as ING1, which is a tumor suppressor gene candidate. See Garkavtsev, et al., Nature 391: 295–8 (1998), incorporated by reference. The sequence found in the breast cancer library, differed from the known sequence of ING1 at six residues, i.e., positions 818, 836, 855, 861, 866 and 874. The sequence with the six variants is set forth at SEQ ID NO: 1. The sequence of wild type ING1 is set out at SEQ ID NO: 2.

To determine if any of these differences represented a mutation in tumors, a short, PCR fragment which contained the six positions referred to supra was amplified from a panel of allogeneic normal tissue, subdloned, amplified, and sequenced following standard methods.

The results indicated that the sequences in the allogeneic tissues were identical to what * was found in tumors, ruling out the hypothesis that the sequence differences were a tumor associated mutation. This conclusion was confirmed, using the testicular library clone, and using restriction analysis of ING1 cDNA taken from normal tissues. One must conclude, therefore, that the sequence information provided by Garkavtsev, et al., supra, is correct.

Example 4

Additional experiments were carried out to determine whether genetic variations might exist in the 5' portion of the ING1 gene, which might differ from the 5' portion of the clone discussed supra (SEQ ED NO: 1). In a first group of experiments, attempts were made to obtain full length ING1 cDNA from both the breast tumor library, and the testicular library. SEQ ID NO: 1 was used as a probe of the library, using standard methods.

Four clones were isolated from the testicular library and none were isolated from the breast cancer library. The four clones, following sequencing, were found to derive from three transcript variants. The three variants were identical from position 586 down to their 3' end, but differed in their 5' regions, suggesting alternatively spliced variants, involving the same exon-intron junction. All three differed from the sequence of ING1 described by Garkavtsev, et al., in Nat. Genet. 14: 415–420 (1996). These three variants are set out as SEQ ID NOS: 1, 3 and 4.

All of the sequences were then analyzed. The ORFs of SEQ ID NOS: 2, 1 and 4 (SEQ ID NO: 2 is the originally disclosed, ING1 sequence), encode polypeptides of 294,279 and 235 amino acids, of which 233 are encoded by the 3' region common to the three sequences. These putative sequences are set out as SEQ ID NOS: 19, 5, and 7. With respect to SEQ ID NO: 3, however, no translational initiation site could be identified in its 5' region.

Example 5

The data regarding SEQ ID NO: 3, described supra, suggested further experiments to find additional ORFs in the 5-end of variant transcripts of the molecule. In order to determine this, 5'-RACE-PCR was carried out using gene specific and adapted specific primers, together with commercially available products, and standard methodologies.

The primers used for these experiments were:
CACACAGGATCCATGTTGAGTCCTGCCAACGG
CGTGGTCGTGGTTGCTGGACGCG
(SEQ ID NOS: 9 and 10), for SEQ ID NO: 1;
CCCAGCGGCCCTGACGCTGTC
CGTGGTCGTGGTTGCTGGACGCG
(SEQ ID NOS: 11 and 12), for SEQ ID NO: 3; and
GGAAGAGATAAGGCCTAGGGAAG
CGTGGTCGTGGTTGCTGGACGCG
(SEQ ID NOS: 13 and 14), for SEQ ID NO: 4.

Cloning and sequencing of the products of RACE PCR showed that the variant sequence of SEQ ID NO: 4 was 5' to SEQ ID NO: 5, and that full length cDNA for the variant SEQ ID NO: 3 contained an additional exon 609 nucleotides long, positioned between SEQ ID NO: 3 and the shared, 3' sequence referred to supra. This exon did not include an ORF. The first available initiation site would be an initial methionine at amino acid 70 of SEQ ID NO: 1. Thus, if expressed, SEQ ID NO: 3 would correspond to a molecule with a 681 base pair, untranslated 5' end and a region encoding 210 amino acids. This is SEQ ID NO: 6.

Example 6

The presence of transcript variants with at least 3 different transcriptional initiation sites, and possibly different promoters, suggested that mRNA expression might be under different, tissue specific regulation.

To determine this, variant-specific primers were synthesized, and RT-PCR was carried out on a panel of tissues, using standard methods.

SEQ ID NO: 1 was found to be expressed universally in all of the normal breast, brain and testis tissues examined, in six breast cancer lines, and 8 melanoma cell lines, and in cultured melanocytes. SEQ ID NO: 3 was found to be expressed in four of the six breast cancer lines, normal testis, liver, kidney, colon and brain. SEQ ID NO: 4 was only found to be expressed by normal testis cells and weakly in brain cells.

Example 7

A further set of experiments were carried out to determine if antibodies against ING1 were present in sera of normal and cancer patients. A phase plaque immuno assay of the type described supra was carried out, using clones of SEQ ID NO: 1 as target. Of 14 allogeneic sera taken from breast cancer patients, two were positive at 1:200 dilutions. All normal sera were negative.

Example 8

The R11 cDNA library described supra was then screened using SEQ ID NO: 1 and standard methodologies. A 593 base pair cDNA was identified, which was different from any sequences in the data banks consulted. The sequence of this cDNA is included in SEQ ID NO: 8.

The cDNA molecule set forth as SEQ ID NO: 1 was then used in Southern blotting experiments. In brief, genomic DNA was isolated from normal human tissue, digested with BamHI or Hind III, and then separated onto 0.7% agarose gel, blotted onto nitrocellulose filters, and hybridized using $^{32}$P labelled SEQ ID NO: 1, at high stringency conditions (aqueous buffer, 65° C.). The probes were permitted to hybridize overnight, and then exposed for autoradiography. Two hybridizing DNA species were identified, i.e., SEQ ID NOS: 1 and 8.

Example 9

The cDNA molecule set forth in SEQ ID NO: 8 was then analyzed. 5'-RACE PCR was carried out using normal fetus cDNA. Full length cDNA for the molecule is 772 base pairs long, without the poly A tail. It shows strong homology to SEQ ID NO: 1, with the strongest homology in the 5' two-thirds (76% identity over nucleotide 1–480); however, the longest ORF is only 129 base pairs, and would encode a poly peptide 42 amino acids long which was homologous to, but much shorter than, the expected expression product of SEQ ID NO: 1.

In addition to the coding region, SEQ ID NO: 8 contains 203 base pairs of 5'-untranslated region, and 439 base pairs of 3'-untranslated region.

RT-PCR assays were carried out, as described supra. All of the normal tissues tested, including brain, colon, testis, tissue and breast, were positive for expression of this gene. Eight melanoma cell lines were tested, of which seven showed varying levels of expression, and one showed no expression. Six breast cancer cell lines were tested, of which four showed various levels of expression, and two showed no expression.

Example 10

An additional breast cancer cDNA library, referred to as "BR17-128", was screened, using autologous sera. A cDNA molecule was identified.

Analysis of the sequence suggested that it was incomplete at the 5' end. To extend the sequence, a testicular cDNA library was screened with a nucleotide probe based upon the partial sequence identified in the breast cancer library. An additional 1200 base pairs were identified following these screenings. The 2011 base pairs of information are set forth in SEQ ID NO: 15.

The longest open reading frame is 1539 base pairs, corresponding to a protein of about 59.15 kilodaltons. The deduced sequence is set forth at SEQ ID NO: 16.

RT-PCR was then carried out using the following primers:
CACACAGGATCCATGCAGGCCCCGCACAAGGAG
CACACAAAGCTTCTAGGATTTGGCA-CAGCCAGAG
(SEQ ID NOS: 17 and 18)

Strong signals were observed in normal testis and breast tissue, and weak expression was observed in placenta.

No expression was found in normal brain, kidney, liver, colon, adrenal, fetal brain, lung, pancreas, prostate, thymus, uterus, and ovary tissue of tumor cell lines tested, 2 of the breast cancer lines were strongly positive and two were weakly positive. Of melanoma two of 8 were strongly positive, and 3 were weakly positive. Of lung cancer cell lines, 4 of 15 were strongly positive, and 3 were weakly positive.

When cancer tissue specimens were tested, 16 of 25 breast cancer samples were strongly positive, and 3 additional samples were weakly positive. Two of 36 melanoma samples were positive (one strong, one weak). All other cancer tissue samples were negative.

When Northern blotting was carried out, a high molecular weight smear was observed in testis, but in no other tissues tested.

The foregoing examples describe the isolation of a nucleic acid molecule which encodes a cancer associated antigen. "Associated" is used herein because while it is clear that the relevant molecule was expressed by several types of cancer, other cancers, not screened herein, may also express the antigen.

The invention relates to nucleic acid molecules which encode the antigens encoded by, e.g., SEQ ID NOS: 1, 3, 8, and 15, as well as the antigens encoded thereby, such as the proteins with the amino acid sequences of SEQ ID NOS: 5, 6, 7, 16 and 19. It is to be understood that all sequences which encode the recited antigen are a part of the invention.

Also a part of the invention are expression vectors which incorporate the nucleic acid molecules of the invention, in operable linkage (i.e., "operably linked") to a promoter. Construction of such vectors, such as viral (e.g., adenovirus or Vaccinia virus) or attenuated viral vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera*

*frugiperda*), NIH 3T3 cells, and so forth. Prokaryotic cells, such as *E. coli* and other bacteria may also be used. Any of these cells can also be transformed or transfected with further nucleic acid molecules, such as those encoding cytokines, e.g., interleukins such as IL-2, 4, 6, or 12 or HLA or MHC molecules.

Also a part of the invention are the antigens described herein, both in original form and in any different post translational modified forms. The molecules are large enough to be antigenic without any post translational modification, and hence are useful as immunogens, when a combined with an adjuvant (or without it), in both precursor and post-translationally modified forms. Antibodies produced using these antigens, both poly and monoclonal, are also a part of the invention as well as hybridomas which make monoclonal antibodies to the antigens. The whole protein can be used therapeutically, or in portions, as discussed infra. Also a part of the invention are antibodies against this antigen, be these polyclonal, monoclonal, reactive fragments, such as Fab, (F(ab)$_2$' and other fragments, as well as chimeras, humanized antibodies, recombinantly produced antibodies, and so forth.

As is clear from the disclosure, one may use the proteins and nucleic acid molecules of the invention diagnostically. The SEREX methodology discussed herein is premised on an immune response to a pathology associated antigen. Hence, one may assay for the relevant pathology via, e.g., testing a body fluid sample of a subject, such as serum, for reactivity with the antigen per se. Reactivity would be deemed indicative of possible presence of the pathology. So, too, could one assay for the expression of any of the antigens via any of the standard nucleic acid hybridization assays which are well known to the art, and need not be elaborated upon herein. One could assay for antibodies against the subject molecules, using standard immunoassays as well.

Analysis of SEQ ID NO: 1, 3, 4, 8, and 15 will show that there are 5' and 3' non-coding regions presented therein. The invention relates to those isolated nucleic acid molecules which contain at least the coding segment, and which may contain any or all of the non-coding 5' and 3' portions.

Also a part of the invention are portions of the relevant nucleic acid molecules which can be used, for example, as oligonucleotide primers and/or probes, such as one or more of SEQ ID NOS: 9, 10, 11, 12, 13, 14, 17 and 18, as well as amplification product like nucleic acid molecules comprising at least nucleotides 305–748 of SEQ ID NO: 1.

As was discussed supra, study of other members of the "CT" family reveals that these are also processed to peptides which provoke lysis by cytolytic T cells. There has been a great deal of work on motifs for various MHC or HLA molecules, which is applicable here. Hence, a further aspect of the invention is a therapeutic method, wherein one or more peptides derived from the antigens of the invention which bind to an HLA molecule on the surface of a patient's tumor cells are administered to the patient, in an amount sufficient for the peptides to bind to the MHC/HLA molecules, and provoke lysis by T cells. Any combination of peptides may be used. These peptides, which may be used alone or in combination, as well as the entire protein or immunoreactive portions thereof, may be administered to a subject in need thereof, using any of the standard types of administration, such as intravenous, intradermal, subcutaneous, oral, rectal, and transdermal administration. Standard pharmaceutical carriers, adjuvants, such as saponins, GM-CSF, and interleukins and so forth may also be used. Further, these peptides and proteins may be formulated into vaccines with the listed material, as may dendritic cells, or other cells which present relevant MHC/peptide complexes.

Similarly, the invention contemplates therapies wherein nucleic acid molecules which encode the proteins of the invention, one or more or peptides which are derived from these proteins are incorporated into a vector, such as a Vaccinia or adenovirus based vector, to render it transfectable into eukaryotic cells, such as human cells. Similarly, nucleic acid molecules which encode one or more of the peptides may be incorporated into these vectors, which are then the major constituent of nucleic acid bases therapies.

Any of these assays can also be used in progression/regression studies. One can monitor the course of abnormality involving expression of these antigens simply by monitoring levels of the protein, its expression, antibodies against it and so forth using any or all of the methods set forth supra.

It should be clear that these methodologies may also be used to track the efficacy of a therapeutic regime. Essentially, one can take a baseline value for a protein of interest using any of the assays discussed supra, administer a given therapeutic agent, and then monitor levels of the protein thereafter, observing changes in antigen levels as indicia of the efficacy of the regime.

As was indicated supra, the invention involves, inter alia, the recognition of an "integrated" immune response to the molecules of the invention. One ramification of this is the ability to monitor the course of cancer therapy. In this method, which is a part of the invention, a subject in need of the therapy receives a vaccination of a type described herein. Such a vaccination results, e.g., in a T cell response against cells presenting HLA/peptide complexes on their cells. The response also includes an antibody response, possibly a result of the release of antibody provoking proteins via the lysis of cells by the T cells. Hence, one can monitor the effect of a vaccine, by monitoring an antibody response. As is indicated, supra, an increase in antibody titer may be taken as an indicia of progress with a vaccine, and vice versa. Hence, a further aspect of the invention is a method for monitoring efficacy of a vaccine, following administration thereof, by determining levels of antibodies in the subject which are specific for the vaccine itself, or a large molecule of which the vaccine is a part.

The identification of the subject proteins as being implicated in pathological conditions such as cancer also suggests a number of therapeutic approaches in addition to those discussed supra. The experiments set forth supra establish that antibodies are produced in response to expression of the protein. Hence, a further embodiment of the invention is the treatment of conditions which are characterized by aberrant or abnormal levels of one or more of the proteins, via administration of antibodies, such as humanized antibodies, antibody fragments, and so forth. These may be tagged or labelled with appropriate cystostatic or cytotoxic reagents.

T cells may also be administered. It is to be noted that the T cells may be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response, such as the epitopes discussed supra.

The therapeutic approaches may also include antisense therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccine, such as in viral vectors (e.g., Vaccinia), bacterial constructs, such as variants of the known BCG vaccine, and so forth.

Other features and applications of the invention will be clear to the skilled artisan, and need not be set forth herein.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An isolated nucleic acid molecule, the complementary sequence of which hybridizes fully, under highly stringent conditions (aqueous buffer, 65° C.) to the nucleotide sequences set forth in SEQ ID NO: 15, wherein said nucleic acid molecule encodes a cancer associated antigen, wherein said cancer associated antigen is a protein which, when expressed by a human, elicits a humoral response by said human against said protein.

2. An isolated nucleic acid molecule comprising the nucleotide sequence of SEQ ID NO: 15.

3. An isolated nucleic acid molecule comprising the nucleotide sequence of SEQ ID NO: 8.

4. An isolated nucleic acid molecule comprising the nucleotide sequence of SEQ ID NO: 4.

5. An isolated nucleic acid molecule comprising a nucleotide sequence which encodes a protein comprising the amino acid sequence of SEQ ID NO: 16.

6. Expression vector comprising the isolated nucleic acid molecule of claim 1, operably linked to a promoter.

7. Recombinant cell, transformed or transfected with the isolated nucleic acid molecule of claim 2.

8. Recombinant cell, transformed or transfected with the isolated nucleic acid molecule of claim 1.

9. The recombinant cell of claim 7, wherein said recombinant cell is further transfected with a nucleic acid molecule encoding a cytokine, or an MHC molecule.

10. The recombinant cell of claim 8, wherein said recombinant cell is further transfected with a nucleic acid molecule which encodes a cytokine, or an MHC molecule.

11. The recombinant cell of claim 9, wherein said cytokine is an interleukin.

12. The recombinant cell of claim 10, wherein said cytokine is an interleukin.

13. The recombinant cell of claim 11, wherein said interleukin is IL-2, IL-4, or IL-12.

14. The recombinant cell of claim 12, wherein said interleukin is IL-2, IL-4, or IL-12.

15. The recombinant cell of claim 7, rendered non-proliferative.

16. The recombinant cell of claim 8, rendered non-proliferative.

17. The expression vector of claim 6, comprising a mutated or attenuated virus.

18. The expression vector of claim 17, wherein said virus is vaccinia virus or adenovirus.

* * * * *

SEQUENCE LISTING

```
<160> NUMBER OF SEQ ID NOS: 19

<210> SEQ ID NO 1
<211> LENGTH: 1533
<212> TYPE: DNA
<213> ORGANISM: Homo sapiens
<220> FEATURE:
<221> NAME/KEY: CDS
<222> LOCATION: 235
<223> OTHER INFORMATION: unknown

<400> SEQUENCE: 1
ggttttccac gttggacaag tgcggctcgg cggccagcgg agcgcgcccc ttcccgctgc      60
ccgctccgct cctctcttct acccagccca gtgggcgagt gggcagcggc ggccgcggcg     120
ctgggccctc tcccgccggt gtgtgcgcgc tcgtacgcgc ggccccggc gccagccccg      180 ccgcctgaga gggggcctgc gccgccgcc ggggcgtgcg cccgggagcc accgncaccg     240
cggcccgcgc cctcaggcgc tggggtcccc gcggacccgg aggcggcgga cgggctcggc     300
agatgtagcc gccgggccga agcaggagcc ggcgggggg cgccgggaga gcgagggctt     360
tgcattttgc agtgctattt tttgagggg gcggagggtg gaggaagtcg gaaagccgcg     420
ccgagtcgcg ggggacctcc ggggtgaacc atgttgagtc ctgccaacgg ggagcagctc     480
cacctggtga actatgtgga ggactacctg gactccatcg agtccctgcc tttcgacttg     540
cagagaaatg tctcgctgat gcgggagatc gacgcgaaat accaagagat cctgaaggag     600
ctagacgagt gctacgagcg cttcagtcgc gagacagacg gggcgcagaa gcggcggatg     660
ctgcactgtg tgcagcgcgc gctgatccgc agccaggagc tgggcgacga gaagatccag     720
atcgtgagcc agatggtgga gctggtggag aaccgcacgc ggcaggtgga cagccacgtg     780
gagctgttcg aggcgcagca ggagctgggc gacacagcgg gcaacagcgg caaggctggc     840
gcggacaggc ccaaaggcga ggcggcagcg caggctgaca agcccaacag caagcgctca     900
cggcggcagc gcaacaacga gaaccgtgag aacgcgtcca gcaaccacga ccacgacgac     960
ggcgcctcgg gcacacccaa ggagaagaag gccaagacct ccaagaagaa gaagcgctcc    1020
aaggccaagg cggagcgaga ggcgtcccct gccgacctcc ccatcgaccc caacgaaccc    1080
acgtactgtc tgtgcaacca ggtctcctat ggggagatga tcggctgcga caacgacgag    1140
tgccccatcg agtggttcca cttctcgtgc gtggggctca atcataaacc caagggcaag    1200
tggtactgtc ccaagtgccg gggggagaac gagaagacca tggacaaagc cctggagaaa    1260
tccaaaaaag agagggctta aacaggtag tttgtggaca ggcgcctggt gtgaggagga    1320
caaaataaac cgtgtattta ttacattgct gcctttgttg aggtgcaagg agtgtaaaat    1380 gtatatttttt aaagaatgtt agaaaggaa ccattccttt catagggatg gcagtgattc    1440
tgtttgcctt ttgttttcat tggtacacgt gtaacaagaa agtggtctgt ggatcagcat    1500
tttagaaact acaaatatag gtttgattca aca                                1533
```

<210> SEQ ID NO 2
<211> LENGTH: 1143
<212> TYPE: DNA
<213> ORGANISM: Homo sapiens

<400> SEQUENCE: 2

| | | | | | |
|---|---|---|---|---|---|
| gagtaacccg | ataatatgcc | gttgtccggc | acggcgacga | gaattcccag | atatagcagt | 60 |
| agcagtgatc | ccgggcctgt | ggctcggggc | cggggctgca | gttcggaccg | cctcccgcga | 120 |
| cccgcggggg | ctcggagaca | gtttcaggcc | gcatctttgc | tgacccgagg | gtggggccgc | 180 |
| gcgtggccgt | ggaaacagat | cctgaaggag | ctagacgagt | gctacgagcg | cttcagtcgc | 240 |
| gagacagacg | gggcgcagaa | gcggcggatg | ctgcactgtg | tgcagcgcgc | gctgatccgc | 300 |
| agccaggagc | tgggcgacga | gaagatccag | atcgtgagcc | agatggtgga | gctggtggag | 360 |
| aaccgcacgc | ggcaggtgga | cagccacgtg | gagctgttcg | aggcgcagca | ggagctgggc | 420 |
| gacacagtgg | gcaacagcgg | caaggttggc | gcggacaggc | ccaatggcga | tgcggtagcg | 480 |
| cagtctgaca | agcccaacag | caagcgctca | cggcggcagc | gcaacaacga | gaaccgtgag | 540 |
| aacgcgtcca | gcaaccacga | ccacgacgac | ggcgcctcgg | gcacacccaa | ggagaagaag | 600 |
| gccaagacct | ccaagaagaa | gaagcgctcc | aaggccaagg | cggagcgaga | ggcgtcccct | 660 |
| gccgacctcc | ccatcgaccc | caacgaaccc | acgtactgtc | tgtgcaacca | ggtctcctat | 720 |
| ggggagatga | tcggctgcga | caacgacgag | tgccccatcg | agtggttcca | cttctcgtgc | 780 |
| gtggggctca | atcataaacc | caaggggcaag | tggtactgtc | ccaagtgccg | ggggagaac | 840 |
| gagaagacca | tggacaaagc | cctggagaaa | tccaaaaaag | agagggctta | caacaggtag | 900 |
| tttgtggaca | ggcgcctggt | gtgaggagga | caaaataaac | cgtgtattta | ttacattgct | 960 |
| gcctttgttg | aggtgcaagg | agtgtaaaat | gtatattttt | aaagaatgtt | agaaaaggaa | 1020 |
| ccattccttt | catagggatg | gcagtgattc | tgtttgcctt | ttgttttcat | tggtacacgt | 1080 |
| gtaacaagaa | agtggtctgt | ggatcagcat | tttagaaact | acaaatatag | gtttgattca | 1140 |
| aca | | | | | 1143 |

<210> SEQ ID NO 3
<211> LENGTH: 742
<212> TYPE: DNA
<213> ORGANISM: Homo sapiens
<220> FEATURE:

<400> SEQUENCE: 3

| | | | | | |
|---|---|---|---|---|---|
| cgccgtccac | accccagcgg | ccctgacgct | gtcccctccg | cgaccctcgc | ctctggaaaa | 60 |
| agtgacaggc | aaggccacgc | ccccgcgagg | gccggcctcg | agcccgcagc | ccccagggcc | 120 |
| tgggacgaga | tcctgaagga | gctagacgag | tgctacgagc | gcttcagtcg | cgagacagac | 180 |
| ggggcgcaga | agcggcggat | gctgcactgt | gtgcagcgcg | cgctgatccg | cagccaggag | 240 |
| ctgggcgacg | agaagatcca | gatcgtgagc | cagatggtgg | agctggtgga | gaaccgcacg | 300 |
| cggcaggtgg | acagccacgt | ggagctgttc | gaggcgcagc | aggagctggg | cgacacagcg | 360 |
| ggcaacagcg | gcaaggctgg | gcgggacagg | cccaaggcg | aggcggcagc | gcaggctgac | 420 |
| aagcccaaca | gcaagcgctc | acggcggcag | cgcaacaacg | agaaccgtga | gaacgcgtcc | 480 |
| agcaaccacg | accacgacga | cggcgcctcg | ggcacaccca | aggagaagaa | ggccaagacc | 540 |
| tccaagaaga | agaagcgctc | caaggccaag | gcggagcgag | aggcgtcccc | tgccgacctc | 600 |
| cccatcgacc | ccaacgaacc | cacgtactgt | ctgtgcaacc | aggtctccta | tggggagatg | 660 |
| atcggctgcg | acaacgacga | gtgccccatc | gagtggttcc | acttctcgtg | cgtggggctc | 720 |

```
aatcataaac ccaagggcaa gt                                              742
```

<210> SEQ ID NO 4
<211> LENGTH: 857
<212> TYPE: DNA
<213> ORGANISM: Homo sapiens

<400> SEQUENCE: 4

```
cctccgagaa cggtgtccat ggcacagggc gggaagagat aaggcctagg gaaggcgccc     60
ctcgggccta tccacctctt ctggggctcg gcactaggaa gcagcttccc tctcaggccc    120
ctttgtctcc aagccgttcc aaactgagta ccgggagacg acacaaaggg agggcggtga    180
cggatggcgc aggcgcggga gccgcctagg ctgctgggag tggtggtccg gccgcggaat    240
ggagatcctg aaggagctag acgagtgcta cgagcgcttc agtcgcgaga cagacggggc    300
gcagaagcgg cggatgctgc actgtgtgca gcgcgcgctg atccgcagcc aggagctggg    360
cgacgagaag atccagatcg tgagccagat ggtggagctg gtggagaacc gcacgcggca    420
ggtggacagc cacgtggagc tgttcgaggc agcaggag ctgggcgaca cagcgggcaa     480
cagcggcaag gctggcgcgg acaggcccaa aggcgaggcg gcagcgcagg ctgacaagcc    540
caacagcaag cgctcacggc ggcagcgcaa caacgagaac cgtgagaacg cgtccagcaa    600
ccacgaccac gacgacggcg cctcgggcac acccaaggag aagaaggcca agacctccaa    660
gaagaagaag cgctccaagg ccaaggcgga gcgagaggcg tcccctgccg acctcccat    720
cgaccccaac gaacccacgt actgtctgtg caaccaggtc tcctatgggg agatgatcgg    780
ctgcgacaac gacgagtgcc ccatcgagtg gttccacttc tcgtgcgtgg ggctcaatca    840
taaacccaag ggcaagt                                                   857
```

<210> SEQ ID NO 5
<211> LENGTH: 279
<212> TYPE: PRT
<213> ORGANISM: Homo sapiens

<400> SEQUENCE: 5

```
Met Leu Ser Pro Ala Asn Gly Glu Gln Leu His Leu Val Asn Tyr Val
1               5                   10                  15

Glu Asp Tyr Leu Asp Ser Ile Glu Ser Leu Pro Phe Asp Leu Gln Arg
            20                  25                  30

Asn Val Ser Leu Met Arg Glu Ile Asp Ala Lys Tyr Gln Glu Ile Leu
        35                  40                  45

Lys Glu Leu Asp Glu Cys Tyr Glu Arg Phe Ser Arg Glu Thr Asp Gly
    50                  55                  60

Ala Gln Lys Arg Arg Met Leu His Cys Val Gln Arg Ala Leu Ile Arg
65                  70                  75                  80

Ser Gln Glu Leu Gly Asp Glu Lys Ile Gln Ile Val Ser Gln Met Val
                85                  90                  95

Glu Leu Val Glu Asn Arg Thr Arg Gln Val Asp Ser His Val Glu Leu
            100                 105                 110

Phe Glu Ala Gln Gln Glu Leu Gly Asp Thr Val Gly Asn Ser Gly Lys
        115                 120                 125

Val Gly Ala Asp Arg Pro Asn Gly Asp Ala Val Ala Gln Ser Asp Lys
    130                 135                 140

Pro Asn Ser Lys Arg Ser Arg Arg Gln Arg Asn Asn Glu Asn Arg Glu
145                 150                 155                 160
```

```
Asn Ala Ser Ser Asn His Asp His Asp Asp Gly Ala Ser Gly Thr Pro
            165                 170                 175

Lys Glu Lys Lys Ala Lys Thr Ser Lys Lys Lys Arg Ser Lys Ala
        180                 185                 190

Lys Ala Glu Arg Glu Ala Ser Pro Ala Asp Leu Pro Ile Asp Pro Asn
        195                 200                 205

Glu Pro Thr Tyr Cys Leu Cys Asn Gln Val Ser Tyr Gly Glu Met Ile
    210                 215                 220

Gly Cys Asp Asn Asp Glu Cys Pro Ile Glu Trp Phe His Phe Ser Cys
225                 230                 235                 240

Val Gly Leu Asn His Lys Pro Lys Gly Lys Trp Tyr Cys Pro Lys Cys
            245                 250                 255

Arg Gly Glu Asn Glu Lys Thr Met Asp Lys Ala Leu Glu Lys Ser Lys
            260                 265                 270

Lys Glu Arg Ala Tyr Asn Arg
        275

<210> SEQ ID NO 6
<211> LENGTH: 210
<212> TYPE: PRT
<213> ORGANISM: Homo sapiens
<220> FEATURE:

<400> SEQUENCE: 6

Met Leu His Cys Val Gln Arg Ala Leu Ile Arg Ser Gln Glu Leu Gly
1               5                   10                  15

Asp Glu Lys Ile Gln Ile Val Ser Gln Met Val Glu Leu Val Glu Asn
            20                  25                  30

Arg Thr Arg Gln Val Asp Ser His Val Glu Leu Phe Glu Ala Gln Gln
        35                  40                  45

Glu Leu Gly Asp Thr Val Gly Asn Ser Gly Lys Val Gly Ala Asp Arg
    50                  55                  60

Pro Asn Gly Asp Ala Val Ala Gln Ser Asp Lys Pro Asn Ser Lys Arg
65                  70                  75                  80

Ser Arg Arg Gln Arg Asn Asn Glu Asn Arg Glu Asn Ala Ser Ser Asn
                85                  90                  95

His Asp His Asp Asp Gly Ala Ser Gly Thr Pro Lys Glu Lys Lys Ala
            100                 105                 110

Lys Thr Ser Lys Lys Lys Arg Ser Lys Ala Lys Ala Glu Arg Glu
        115                 120                 125

Ala Ser Pro Ala Asp Leu Pro Ile Asp Pro Asn Glu Pro Thr Tyr Cys
    130                 135                 140

Leu Cys Asn Gln Val Ser Tyr Gly Glu Met Ile Gly Cys Asp Asn Asp
145                 150                 155                 160

Glu Cys Pro Ile Glu Trp Phe His Phe Ser Cys Val Gly Leu Asn His
                165                 170                 175

Lys Pro Lys Gly Lys Trp Tyr Cys Pro Lys Cys Arg Gly Glu Asn Glu
            180                 185                 190

Lys Thr Met Asp Lys Ala Leu Glu Lys Ser Lys Lys Glu Arg Ala Tyr
        195                 200                 205

Asn Arg
    210

<210> SEQ ID NO 7
<211> LENGTH: 235
<212> TYPE: PRT
```

<213> ORGANISM: Homo sapiens

<400> SEQUENCE: 7

```
Met Glu Ile Leu Lys Glu Leu Asp Glu Cys Tyr Glu Arg Phe Ser Arg
1               5                   10                  15
Glu Thr Asp Gly Ala Gln Lys Arg Arg Met Leu His Cys Val Gln Arg
                20                  25                  30
Ala Leu Ile Arg Ser Gln Glu Leu Gly Asp Glu Lys Ile Gln Ile Val
            35                  40                  45
Ser Gln Met Val Glu Leu Val Glu Asn Arg Thr Arg Gln Val Asp Ser
        50                  55                  60
His Val Glu Leu Phe Glu Ala Gln Gln Glu Leu Gly Asp Thr Val Gly
65                  70                  75                  80
Asn Ser Gly Lys Val Gly Ala Asp Arg Pro Asn Gly Asp Ala Val Ala
                85                  90                  95
Gln Ser Asp Lys Pro Asn Ser Lys Arg Ser Arg Gln Arg Asn Asn
                100                 105                 110
Glu Asn Arg Glu Asn Ala Ser Ser Asn His Asp His Asp Asp Gly Ala
            115                 120                 125
Ser Gly Thr Pro Lys Glu Lys Lys Ala Lys Thr Ser Lys Lys Lys
        130                 135                 140
Arg Ser Lys Ala Lys Ala Glu Arg Glu Ala Ser Pro Ala Asp Leu Pro
145                 150                 155                 160
Ile Asp Pro Asn Glu Pro Thr Tyr Cys Leu Cys Asn Gln Val Ser Tyr
                165                 170                 175
Gly Glu Met Ile Gly Cys Asp Asn Asp Glu Cys Pro Ile Glu Trp Phe
            180                 185                 190
His Phe Ser Cys Val Gly Leu Asn His Lys Pro Lys Gly Lys Trp Tyr
        195                 200                 205
Cys Pro Lys Cys Arg Gly Glu Asn Glu Lys Thr Met Asp Lys Ala Leu
    210                 215                 220
Glu Lys Ser Lys Lys Glu Arg Ala Tyr Asn Arg
225                 230                 235
```

<210> SEQ ID NO 8
<211> LENGTH: 772
<212> TYPE: DNA
<213> ORGANISM: Homo sapiens
<220> FEATURE:
<221> NAME/KEY: CDS
<222> LOCATION: 689,714
<223> OTHER INFORMATION: unknown nucleotides at positions 689 and 714

<400> SEQUENCE: 8

```
aaagcgttct cggcggcagc gcaacaacta gaaccgtgag aacgcgtcca gcaaccgcga      60
cccacgacga cgtcacctcg ggcacgccca aggagaagaa agcccagacc tctaagaaga     120
agcagggctc catggccaag gcgtagcggc aggcgtcccc cgcagacctc cccatcgacc     180
ccagcgagcc ctcctactgg gagatgatcc gctgcgacaa cgaatgcccc atcgagtggt     240
tccgcttctc gtgtgtgagt ctcaaccata accaaagcg caagtggtac tgttccagat     300
gccggggaaa gaacgatggg caaagccctt gagaagtcca gaaaaaaaac agggcttata     360
acaggtagtt tggggacatg cgtctaatag tgaggagaac aaaataagcc agtgtgttga     420
ttacattgcc acctttgctg aggtgcagga agtgtaaaat gtatattttt aaagaatgtt     480
gttagaggcc gggcgcggtg gctcacgcct gtaatcccag cactttggga ggccgaggcg     540
```

```
gtcggatcac gaggtcagga gatcgagacc atcctggcta acacggtgaa accccgtctc      600
tactaaaaat tcaaaaaaaa aattagctgg gcgtggtggc gggcgcctgt agtcccagct      660
attcgggagg ctgaggcagg agaatggcnt gaacctggga ggtggagctt gcantgagcc      720
aaggtcgcgc cactgcactc cagcctgggc gacagagcga gactccatct ta             772
```

```
<210> SEQ ID NO 9
<211> LENGTH: 32
<212> TYPE: DNA
<213> ORGANISM: Homo sapiens

<400> SEQUENCE: 9
cacacaggat ccatgttgag tcctgccaac gg                                   32

<210> SEQ ID NO 10
<211> LENGTH: 23
<212> TYPE: DNA
<213> ORGANISM: Homo sapiens

<400> SEQUENCE: 10
cgtggtcgtg gttgctggac gcg                                             23

<210> SEQ ID NO 11
<211> LENGTH: 21
<212> TYPE: DNA
<213> ORGANISM: Homo sapiens

<400> SEQUENCE: 11
cccagcggcc ctgacgctgt c                                               21

<210> SEQ ID NO 12
<211> LENGTH: 23
<212> TYPE: DNA
<213> ORGANISM: Homo sapiens

<400> SEQUENCE: 12
cgtggtcgtg gttgctggac gcg                                             23

<210> SEQ ID NO 13
<211> LENGTH: 23
<212> TYPE: DNA
<213> ORGANISM: Homo sapiens

<400> SEQUENCE: 13
ggaagagata aggcctaggg aag                                             23

<210> SEQ ID NO 14
<211> LENGTH: 23
<212> TYPE: DNA
<213> ORGANISM: Homo sapiens

<400> SEQUENCE: 14
cgtggtcgtg gttgctggac gcg                                             23

<210> SEQ ID NO 15
<211> LENGTH: 2030
<212> TYPE: DNA
<213> ORGANISM: Homo sapiens
<220> FEATURE:
<221> NAME/KEY: CDS
<222> LOCATION: 1628, 1752, 1758, 1769, 1789, 1873, 1908, 1915, 1933,
      1970, 1976, 2022
<223> OTHER INFORMATION: unknown nucleotides at positions 1628, 1752,
      1758, 1769, 1789, 1873, 1908, 1915, 1933, 1970, 1976, and 2022
```

<400> SEQUENCE: 15

```
ctcgtgccgt taaagatggt cttctgaagg ctaactgcgg aatgaaagtt tctattccaa      60
ctaaagcctt agaattgatg gacatgcaaa ctttcaaagc agagcctccc gagaagccat     120
ctgccttcga gcctgccatt gaaatgcaaa agtctgttcc aaataaagcc ttggaattga     180
agaatgaaca acattgaga gcagatgaga tactcccatc agaatccaaa caaaaggact     240
atgaagaaag ttcttgggat tctgagagtc tctgtgagac tgtttcacag aaggatgtgt     300
gtttacccaa ggctacacat caaaaagaaa tagataaaat aaatgaaaaa ttagaagagt     360
ctcctgataa tgatggtttt ctgaaggctc cctgcagaat gaaagtttct attccaacta     420
aagccttaga attgatggac atgcaaactt caaagcaga gcctcccgag aagccatctg     480
ccttcgagcc tgccattgaa atgcaaaagt ctgttccaaa taaagccttg gaattgaaga     540
atgaacaaac attgagagca gatcagatgt tcccttcaga atcaaaacaa agaaggttg     600
aagaaaattc ttgggattct gagagtctcc gtgagactgt ttcacagaag gatgtgtgtg     660
tacccaaggc tacacatcaa aaagaaatgg ataaaataag tggaaaatta gaagattcaa     720
ctagcctatc aaaaatcttg gatacagttc attcttgtga aagagcaagg gaacttcaaa     780
aagatcactg tgaacaacgt acaggaaaaa tggaacaaat gaaaagaag ttttgtgtac     840
tgaaaaagaa actgtcagaa gcaaagaaa taaaatcaca gttagagaac caaaaagtta     900
aatgggaaca agagctctgc agtgtgagat tgactttaaa ccaagaagaa gagaagagaa     960
gaaatgccga tatattaaat gaaaaatta gggaagaatt aggaagaatc gaagagcagc    1020
ataggaaaga gttagaagtg aaacaacaac ttgaacaggc tctcagaata caagatatag    1080
aattgaagag tgtagaaagt aatttgaatc aggtttctca cactcatgaa atgaaaatt    1140
atctcttaca tgaaaattgc atgttgaaaa aggaaattgc catgctaaaa ctggaaatag    1200
ccacactgaa acaccaatac caggaaaagg aaaataaata ctttgaggac attaagattt    1260
taaaagaaaa gaatgctgaa cttcagatga ccctaaaact gaaagaggaa tcattaacta    1320
aaagggcatc tcaatatagt gggcagctta agttctgat agctgagaac acaatgctca    1380
cttctaaatt gaaggaaaaa caagacaaag aaatactaga ggcagaaatt gaatcacacc    1440
atcctagact ggcttctgct gtacaagacc atgatcaaat tgtgacatca agaaaaagtc    1500
aagaacctgc tttccacatt gcaggagatg cttgtttgca agaaaaatg aatgttgatg    1560
tgagtagtac cgatatataa caatgaggtg ctccatcaac cactttctga gctcaaagg    1620
aaatccanaa gcctaaaaat taatctcaat tatgcaggag atgctctaag agaaaataca    1680
ttggtttcag gaacatgcac aaagagacca acgtgaaaca cagtgtcaaa tgaaggaagc    1740
tgaacacatg tntcaaancg aacaagatna tgtgaacaaa cacactganc agcaggagtc    1800
tctagatcag aaattatttc aactacaaag caaaatatg tggcttcaac agcaattagt    1860
tcatgcacat aangaaagct gacaacaaaa gcaagataac aattgatntt cattntcttg    1920
agaggaaaat gcncatcatc ttctaaaaga gaaaaatgag gagatatttn attacnataa    1980
ccatttaaaa aacccgtata tttcaatatg gaaaaaaaaa anaaaaaaaa                2030
```

<210> SEQ ID NO 16
<211> LENGTH: 512
<212> TYPE: PRT
<213> ORGANISM: Homo sapiens

<400> SEQUENCE: 16

```
Met Lys Val Ser Ile Pro Thr Lys Ala Leu Glu Leu Met Asp Met Gln
1               5                   10                  15

Thr Phe Lys Ala Glu Pro Pro Glu Lys Pro Ser Ala Phe Glu Pro Ala
                20                  25                  30

Ile Glu Met Gln Lys Ser Val Pro Asn Lys Ala Leu Glu Leu Lys Asn
                35                  40                  45

Glu Gln Thr Leu Arg Ala Asp Glu Ile Leu Pro Ser Glu Ser Lys Gln
        50                  55                  60

Lys Asp Tyr Glu Glu Ser Ser Trp Asp Ser Glu Ser Leu Cys Glu Thr
65                  70                  75                  80

Val Ser Gln Lys Asp Val Cys Leu Pro Lys Ala Thr His Gln Lys Glu
                85                  90                  95

Ile Asp Lys Ile Asn Gly Lys Leu Glu Glu Ser Pro Asp Asn Asp Gly
                100                 105                 110

Phe Leu Lys Ala Pro Cys Arg Met Lys Val Ser Ile Pro Thr Lys Ala
                115                 120                 125

Leu Glu Leu Met Asp Met Gln Thr Phe Lys Ala Glu Pro Pro Glu Lys
        130                 135                 140

Pro Ser Ala Phe Glu Pro Ala Ile Glu Met Gln Lys Ser Val Pro Asn
145                 150                 155                 160

Lys Ala Leu Glu Leu Lys Asn Glu Gln Thr Leu Arg Ala Asp Gln Met
                165                 170                 175

Phe Pro Ser Glu Ser Lys Gln Lys Val Glu Glu Asn Ser Trp Asp
                180                 185                 190

Ser Glu Ser Leu Arg Glu Thr Val Ser Gln Lys Asp Val Cys Val Pro
                195                 200                 205

Lys Ala Thr His Gln Lys Glu Met Asp Lys Ile Ser Gly Lys Leu Glu
                210                 215                 220

Asp Ser Thr Ser Leu Ser Lys Ile Leu Asp Thr Val His Ser Cys Glu
225                 230                 235                 240

Arg Ala Arg Glu Leu Gln Lys Asp His Cys Glu Gln Arg Thr Gly Lys
                245                 250                 255

Met Glu Gln Met Lys Lys Phe Cys Val Leu Lys Lys Lys Leu Ser
                260                 265                 270

Glu Ala Lys Glu Ile Lys Ser Gln Leu Glu Asn Gln Lys Val Lys Trp
                275                 280                 285

Glu Gln Glu Leu Cys Ser Val Arg Leu Thr Leu Asn Gln Glu Glu Glu
        290                 295                 300

Lys Arg Arg Asn Ala Asp Ile Leu Asn Glu Lys Ile Arg Glu Glu Leu
305                 310                 315                 320

Gly Arg Ile Glu Glu Gln His Arg Lys Glu Leu Glu Val Lys Gln Gln
                325                 330                 335

Leu Glu Gln Ala Leu Arg Ile Gln Asp Ile Glu Leu Lys Ser Val Glu
                340                 345                 350

Ser Asn Leu Asn Gln Val Ser His Thr His Glu Asn Glu Asn Tyr Leu
                355                 360                 365

Leu His Glu Asn Cys Met Leu Lys Lys Glu Ile Ala Met Leu Lys Leu
        370                 375                 380

Glu Ile Ala Thr Leu Lys His Gln Tyr Gln Glu Lys Glu Asn Lys Tyr
385                 390                 395                 400

Phe Glu Asp Ile Lys Ile Leu Lys Glu Lys Asn Ala Glu Leu Gln Met
                405                 410                 415

Thr Leu Lys Leu Lys Glu Glu Ser Leu Thr Lys Arg Ala Ser Gln Tyr
```

```
                420             425             430
Ser Gly Gln Leu Lys Val Leu Ile Ala Glu Asn Thr Met Leu Thr Ser
        435                 440                 445
Lys Leu Lys Glu Lys Gln Asp Lys Glu Ile Leu Glu Ala Glu Ile Glu
        450                 455                 460
Ser His His Pro Arg Leu Ala Ser Ala Val Gln Asp His Asp Gln Ile
465                 470                 475                 480
Val Thr Ser Arg Lys Ser Gln Glu Pro Ala Phe His Ile Ala Gly Asp
                485                 490                 495
Ala Cys Leu Gln Arg Lys Met Asn Val Asp Val Ser Ser Thr Asp Ile
        500                 505                 510

<210> SEQ ID NO 17
<211> LENGTH: 33
<212> TYPE: DNA
<213> ORGANISM: Homo sapiens

<400> SEQUENCE: 17
cacacaggat ccatgcaggc cccgcacaag gag                               33

<210> SEQ ID NO 18
<211> LENGTH: 34
<212> TYPE: DNA
<213> ORGANISM: Homo sapiens

<400> SEQUENCE: 18
cacacaaagc ttctaggatt tggcacagcc agag                              34

<210> SEQ ID NO 19
<211> LENGTH: 294
<212> TYPE: PRT
<213> ORGANISM: Homo sapiens

<400> SEQUENCE: 19

Met Pro Leu Cys Thr Ala Thr Arg Ile Pro Arg Tyr Ser Ser Ser Ser
1               5                   10                  15
Asp Pro Gly Pro Val Ala Arg Gly Arg Gly Cys Ser Ser Asp Arg Leu
                20                  25                  30
Pro Arg Pro Ala Gly Pro Ala Arg Arg Gln Phe Gln Ala Ala Ser Leu
        35                  40                  45
Leu Thr Arg Gly Trp Gly Arg Ala Trp Pro Trp Lys Gln Ile Leu Lys
        50                  55                  60
Glu Leu Asp Glu Cys Tyr Glu Arg Phe Ser Arg Glu Thr Asp Gly Ala
65                  70                  75                  80
Gln Lys Arg Arg Met Leu His Cys Val Gln Arg Ala Leu Ile Arg Ser
                85                  90                  95
Gln Glu Leu Gly Asp Glu Lys Ile Gln Ile Val Ser Gln Met Val Glu
                100                 105                 110
Leu Val Glu Asn Arg Thr Arg Gln Val Asp Ser His Val Glu Leu Phe
        115                 120                 125
Glu Ala Gln Gln Glu Leu Gly Asp Thr Val Gly Asn Ser Gly Lys Val
        130                 135                 140
Gly Ala Asp Arg Pro Asn Gly Asp Ala Val Ala Gln Ser Asp Lys Pro
145                 150                 155                 160
Asn Ser Lys Arg Ser Arg Arg Gln Arg Asn Asn Glu Asn Arg Glu Asn
                165                 170                 175
Ala Ser Ser Asn His Asp His Asp Asp Gly Ala Ser Gly Thr Pro Lys
```

-continued

```
                    180                 185                 190
Glu Lys Lys Ala Lys Thr Ser Lys Lys Lys Arg Ser Lys Ala Lys
        195                 200                 205

Ala Glu Arg Glu Ala Ser Pro Ala Asp Leu Pro Ile Asp Pro Asn Glu
    210                 215                 220

Pro Thr Tyr Cys Leu Cys Asn Gln Val Ser Tyr Gly Glu Met Ile Gly
225                     230                 235                 240

Cys Asp Asn Asp Glu Cys Pro Ile Glu Trp Phe His Phe Ser Cys Val
                245                 250                 255

Gly Leu Asn His Lys Pro Lys Gly Lys Trp Tyr Cys Pro Lys Cys Arg
            260                 265                 270

Gly Glu Asn Glu Lys Thr Met Asp Lys Ala Leu Glu Lys Ser Lys Lys
        275                 280                 285

Glu Arg Ala Tyr Asn Arg
    290
```